(12) United States Patent
Viljanen et al.

(10) Patent No.: US 6,443,153 B1
(45) Date of Patent: Sep. 3, 2002

(54) ARRANGEMENT IN PROTECTIVE DEVICE

(75) Inventors: Lasse Viljanen, Turku; Jorma Viljanen, Mietoinen, both of (FI)

(73) Assignee: Euromaski Oy, Rauma (FI)

( * ) Notice: Subject to any disclaimer, the term of this patent is extended or adjusted under 35 U.S.C. 154(b) by 0 days.

(21) Appl. No.: 09/509,484

(22) PCT Filed: Sep. 29, 1998

(86) PCT No.: PCT/FI98/00767

§ 371 (c)(1),
(2), (4) Date: Mar. 29, 2000

(87) PCT Pub. No.: WO99/16508

PCT Pub. Date: Apr. 8, 1999

(30) Foreign Application Priority Data

Sep. 30, 1997 (FI) .................................................. 973847

(51) Int. Cl.[7] .............................................. A62B 29/00
(52) U.S. Cl. ............................ 128/205.25; 128/205.22; 128/205.24; 128/206.28
(58) Field of Search ....................... 128/200.24, 201.22, 128/201.23, 201.24, 203.12, 203.29, 204.18, 205.22, 205.24, 205.25, 206.21, 206.28, 207.17, 200.28

(56) References Cited

U.S. PATENT DOCUMENTS

| 3,921,223 A | | 11/1975 | Hoyecki | |
| 5,133,344 A | * | 7/1992 | Jurrius et al. | 128/201.23 |
| 5,265,592 A | * | 11/1993 | Beaussant | 128/201.24 |

FOREIGN PATENT DOCUMENTS

| FI | FI 86031 | | 3/1992 | |
| WO | WO-97/02069 | * | 1/1997 | 128/201.24 |
| WO | WO 98/06458 | | 2/1998 | |

* cited by examiner

Primary Examiner—Glenn K. Dawson
(74) Attorney, Agent, or Firm—Young & Thompson

(57) ABSTRACT

An air breathing arrangement including an air feed inlet and a mask for covering the nose and mouth of a person. The air feed inlet and the mask are connected by a collar which serves as an intermediate storage of air. The collar is shaped to fit around the neck of the person.

5 Claims, 1 Drawing Sheet

ARRANGEMENT IN PROTECTIVE DEVICE

FIELD OF THE INVENTION

The invention relates to an arrangement in a protective device, for instance a welder's mask or a face shield, which comprises means for feeding air from outside the protective device to the person wearing said protective device.

BACKGROUND OF THE INVENTION

To supply the wearer with fresh air for breathing has been a problem with protective devices. The problem is at its worst when the wearer of the protective device has to work in conditions that are hot and involve various fumes and impurities. Various stages of operation relating to welding and grinding can be given as examples of work in which conditions like this prevail.

Attempts have been made to solve the above-described problem by means of various air feed solutions. An example of a typical prior art solution is the one in which air is fed inside a mask or a helmet through a connection arranged in the upper part of the protective device, such as a welder's mask, face shield, safety helmet or some other corresponding device, and is distributed to the facial area of the wearer by means of various nozzle arrangements.

A problem with the above-described prior art technology is, for instance, that the solution is protective-device-specific, and consequently it is difficult to apply the solution to various conventional protective devices. Another problem is the draught generated by air flow, which may in some cases prevent the solution from being utilized completely. The reason for the draught problem is that some people are extremely sensitive to draught, and in any case, continuous air blow directed to eye area, for instance, irritates eyes in a prolonged work situation. A further problem is the weight increase of the protective device due to components required by the solution. Numerically, the weight increase is not large, but it is to be noted that even a slight weight increase may hinder the work, since it is often necessary to wear the protective device for hours without a break, and a weight resting on the head is always a strain on the neck. One more problem is that a shield linked to a helmet prevents the air from being fed from above to the nose and mouth area.

SUMMARY OF THE INVENTION

The object of the invention is to provide an arrangement by means of which the drawbacks of the prior art can be eliminated. This is achieved with an arrangement in accordance with the invention, which is characterized in that the air distribution means comprise a mask part covering the wearer's nose and mouth.

The primary advantage of the invention is that the problems caused by air flow that generates draught to the facial area can be eliminated in a very efficient manner. Another advantage is that the arrangement in accordance with the invention can be used in connection with various protective devices without changes in the protective device itself. Moreover, the arrangement in accordance with the invention supports and protects the wearer's chin, neck and throat without a strain caused by weight. The part acting as the intermediate storage of air also evens out the air flow and ensures a sufficient supply of fresh air. The intermediate storage also acts as a noise reduction element which reduces noise related to the air flow. The arrangement in accordance with the invention also has the advantage that it does not cause any inconvenience whatsoever to eyeglass wearers.

BRIEF DESCRIPTION OF THE DRAWINGS

In the following the invention will be described in greater detail by means of one preferred embodiment shown in the attached drawing, in which.

DETAILED DESCRIPTION OF THE INVENTION

Figure 1:
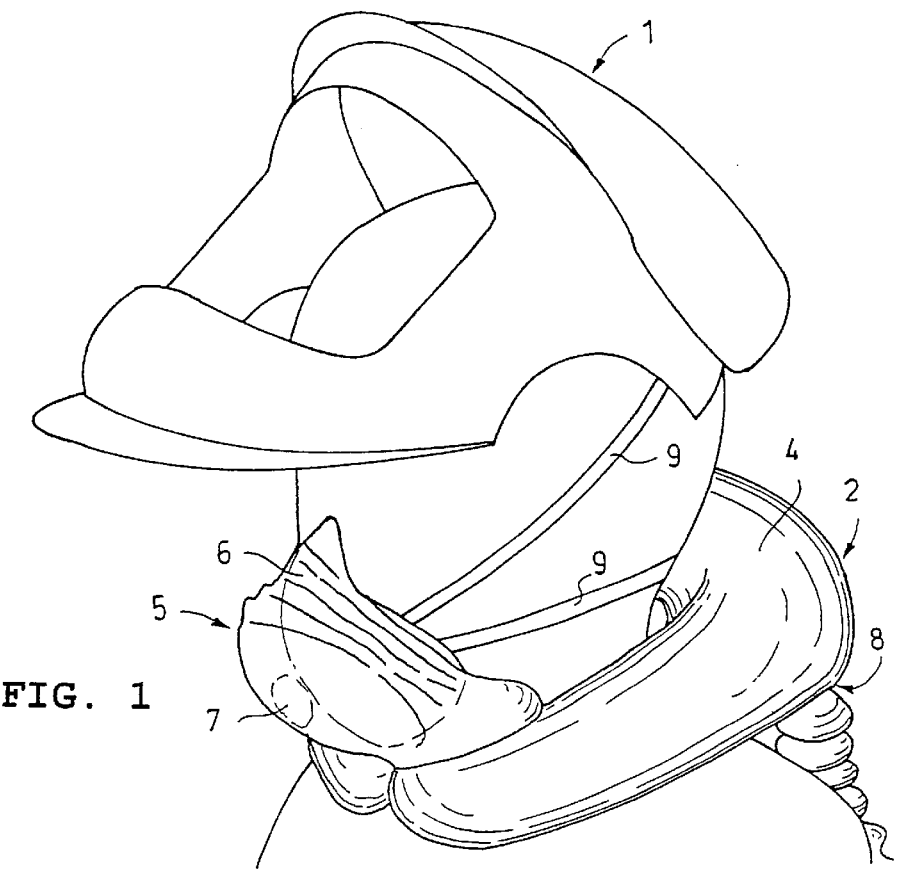
FIG. 1 is a general perspective view of an arrangement in accordance with the invention.
Figure 2:
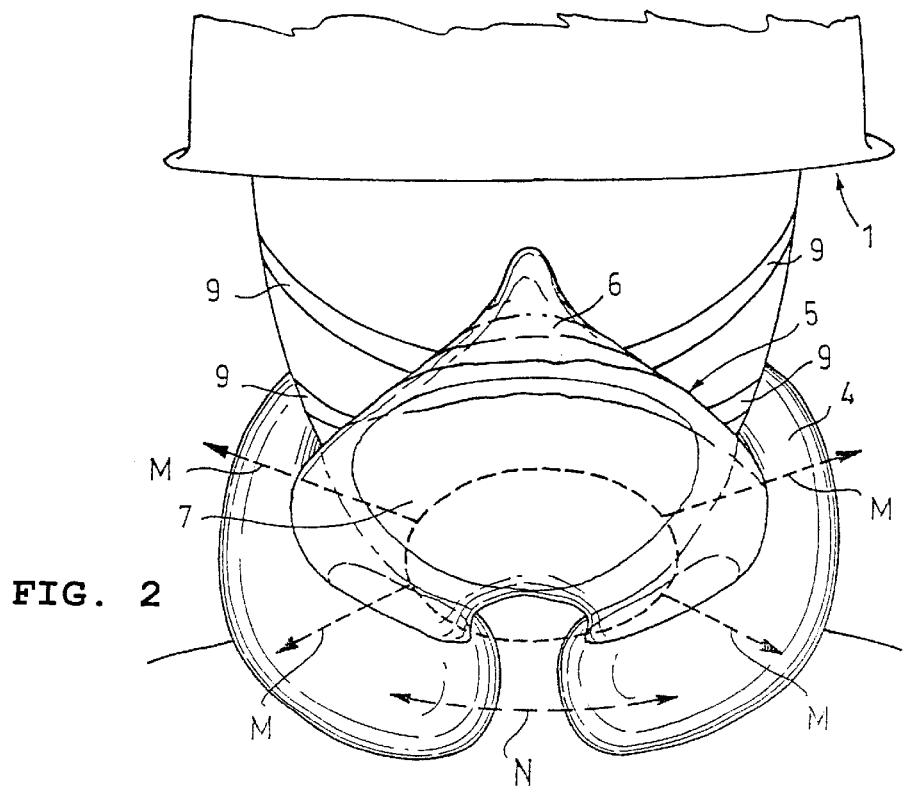
FIG. 2 is a front view of the arrangement of FIG. 1.

In FIGS. 1 and 2, a protective device in general is indicated by the reference numeral 1. The protective device 1 is a welder's mask in the example of the figures, but it is obvious that the protective device 1 may also be some other protective device, for instance, a face shield, a safety helmet with omnidirectional head protection, et cetera.

In the figures, the reference numeral 2 indicates in general means for feeding air from outside the protective device to the person wearing said protective device. The means 2 comprise, for instance, a hose that is connected to a source of air. The source of air may be, for instance, a separate blowing apparatus, a shared air system between users, or some such arrangement. These devices and arrangements are conventional technology to the person skilled in the art, so they are not described in greater detail in this connection.

In accordance with the basic idea of the invention, the means 2 for feeding air also comprise a collar part 4 to be arranged round the wearer's neck, the collar part being arranged to serve as an intermediate storage of air to be fed to the wearer. The intermediate storage of air evens out the flow of air and ensures a sufficient supply of air. In the embodiment of the figures, an air feed inlet 8 is preferably arranged in the back of the collar part 4. To place the inlet in this way is preferable from the wearer's point of view, since the air feed hose interferes as little as possible with working. Air distribution means 5, which are arranged to distribute the air, fed to the collar part 4 acting as the intermediate storage of air, to the facial area of the wearer, are arranged in the collar part 4. The air distribution means 5 preferably comprise a mask part 6 covering the wearer's nose and mouth, by means of which mask part fresh air is supplied directly for breathing in an efficient manner. If necessary, the mask part 6 can be supported in place by means of elastic straps, or the like 9, extending round the wearer's head. The mask part has the advantage that the draught problems caused by air flow can be eliminated in a very efficient manner. A valve means 7 through which the exhaled air is conducted out of the mask part, is arranged in the front of the mask part 6. The flow of the exhaled air is indicated in principle by arrows M in FIG. 2. The valve means 7 may consist of, for instance, a thin film which does not let in air and through which the pressurized air is exhaled out of the mask. Naturally, a suitable flap mechanism, etc., can also be used as the valve means. The valve means can also be made adjustable.

The collar part 4 and the air distribution means 5 are preferably made of a flexible material, e.g. silicone rubber or some other such material. The collar part 4 and the air distribution means 5, for instance the mask part 6, can preferably be of the same material and manufactured to form an integral part, as is done in the example of the figures. However, it is obvious that the collar part 4 and the air distribution means 5 can also be formed into separate elements which are interconnected with an air channel. Due to the flexible, integral structure shown in the figure, the air feed to the mask part can be implemented in a most advantageous manner. The flexible structure also permits flexible and close-fitting support and protection to the wearer's chin, neck and throat. The flexibility of the structure is indicated by the arrow N in FIG. 2.

The above-described embodiment is not intended to restrict the invention in any way, but the invention may be modified quite freely within the scope of the appended claims. Hence it is obvious that the arrangement in accordance with the invention or its details need not necessarily be exactly such as illustrated in the figures, but other solutions are also possible.

What is claimed is:

1. The combination of a protective device and an air breathing arrangement for a person wearing the protective device, the air breathing arrangement comprising:

an air feed inlet;

a mask for covering the nose and mouth of the person; and a generally annular collar connecting the inlet and the mask to distribute air from the inlet to the nose and mouth of the person, the collar shaped and configured to fit only around the neck of the person and acting as an intermediate storage for the air; and wherein the protective device comprises a hood separate from the air breathing arrangement and movable to cover the mask of the air breathing arrangement and protect the face of the person.

2. The combination as claimed in claim 1, wherein the collar and the mask are made of flexible material.

3. The combination as claimed in claim 1, wherein the collar and the mask are interconnected with an air channel.

4. The combination as claimed in claim 1, wherein the collar and the mask are made of the same material and formed as an integral part.

5. The combination as claimed in claim 1, wherein the mask comprises a valve for passage of exhaled air from the person.

* * * * *